United States Patent [19]

Phinney

[11] Patent Number: 5,512,274
[45] Date of Patent: Apr. 30, 1996

[54] METAL HYDROXIDE DEODORANT FORMULATION

[76] Inventor: Robin L. Phinney, 2777 Eastview, Sasktoon, Sasic S7J 3H3, Canada

[21] Appl. No.: 982,099

[22] Filed: Nov. 25, 1992

Related U.S. Application Data

[63] Continuation-in-part of Ser. No. 833,549, Feb. 10, 1992, abandoned.
[51] Int. Cl.⁶ ............................... A61K 7/32; A61K 7/36; A61K 9/12; C09K 19/00
[52] U.S. Cl. .................. 424/65; 424/47; 424/67; 424/68; 424/69; 424/DIG. 5; 514/847; 428/1
[58] Field of Search ................................. 424/65

[56] References Cited

U.S. PATENT DOCUMENTS 2,350,047  5/1944  Klarnann .................................. 429/65

OTHER PUBLICATIONS

Sagarin Cosmetics and Science Technology, Sep. 1957, pp. 717–721.

*Primary Examiner*—Shelley A. Dodson
*Attorney, Agent, or Firm*—Finnegan, Henderson, Farabow, Garrett & Dunner

[57] ABSTRACT

A deodorant composition consists essentially of magnesium hydroxide in an amount sufficient to neutralize 3-methyl-2-hexanoic acid associated with human perspiration. The composition is used by applying it to a surface in contact with human perspiration in an amount sufficient to reduce perspiration odor. The composition and method are useful for inhibiting perspiration odor in humans.

14 Claims, No Drawings

METAL HYDROXIDE DEODORANT FORMULATION

CROSS-REFERENCE TO RELATED APPLICATION

This application is a continuation-in-part of application Ser. No. 07/833,549, filed Feb. 10, 1992, abandoned, the entire disclosure of which is relied upon and incorporated by reference herein.

BACKGROUND

Milk of magnesia or magnesium hydroxide applied in a freshly precipitated form has been found to be an effective deodorant. The milk of magnesia can be evenly applied by a pump spray bottle as a slurry based on a mixture of alcohol and water. It has also been found that a mixture of the hydroxides of zinc and magnesium can provide long lasting protection against odor due to perspiration particularly with a mole excess of magnesia. These materials are active ingredients, and as such can be applied in a variety of ways such as aerosols, moisturizing creams, sticks, sprays and roll-on type applicators with the usual type of scents, softeners, moisturizers and emollients as desired.

The materials of this invention, not previously identified as deodorant agents, provide active hydroxide, in a manner compatible with good skin care, to neutralize 3-methyl-2-hexanoic acid and similar materials that have been demonstrated to be largely responsible for body odor associated with perspiration. These weak organic acids are produced by a bacterial action and require a moderately strong hydroxide type base to neutralize them and eliminate odor associated with, but not confined to perspiration.

Numerous agents have been used to combat perspiration and perspiration odor. As pointed out in U.S. Pat. No. 3,996,346 a range of acidic to neutral to basic salts have been proposed as active ingredients to reduce body odor and/or stem perspiration. Many of the salts cited in the patent can be injurious to the skin. Acid salts such as aluminum chloride, for example, hydrolyze to form hydrochloric acid, which can be injurious to both skin and clothing. Additionally, aluminum has been identified as a potential contributor to Alzheimer Disease. Potassium alum has become widely available, and while effective as a deodorant, it hydrolyzes to form even more injurious sulphuric acid as well as aluminum in a soluble ionic form, which can lead to higher rates of absorption into the body than is the case with aluminum metal or alumina.

These salts have hydrolysis points or protolysis reactions because they hydrolyze at different points on the pH scale (Chemistry of the Elements, Greenwood and Earnshaw, 1984) and precipitate out of solution, primarily as hydroxides, at various pH's. For example, ferric hydroxide precipitates or hydrolyzes out of solution a pH of about 2.6 to 4.0 while aluminum hydroxide precipitates or hydrolyzes out of solution in the range of 3.6 to 4.2.

Other salts, such as zinc, precipitate as hydroxides in the range of 6.5 to 8.0, but salts of these materials can behave in an erratic manner with many individuals in that they work effectively for very irregular periods of time. In addition, zinc sulphate still releases sulphuric acid upon hydrolysis. The sporadic efficacy may be due to lack of hydrolysis, conversion to relatively inactive carbonate or oxide, or some combination of these factors.

Basic materials have been proposed, such as in U.S. Pat. No. 74,871; U.S. Pat. No. 1,558,406; U.S. Pat. No. 2,114,559; and U.S. Pat. No. 2,187,163. There are problems with most of these materials.

The carbonates of U.S. Pat. No. 74,871 are very soluble and quickly leach from the skin during perspiration. Some agents are very basic and could be injurious to the skin.

The active agent of U.S. Pat. No. 1,558,406, a hexametaphosphate, is soluble and liable to be washed away during perspiration. Being a phosphate, this agent could well serve as a major nutrient source of the bacteria believed to be responsible for body odor and this agent could thereby promote body odor rather than diminish it.

U.S. Pat. No. 1,558,405 contains mention of some of the same basic materials mentioned in U.S. Pat. No. 74,781 and includes "sodium bicarbonate, potassium bicarbonate, sodium or potassium carbonate, calcium hydroxide and the like . . . ". The term "and the like" is vague, nebulous, undefined and unspecified given the previous explicit identification of agents. Materials mentioned, such as potassium carbonate and lime, are very basic and could injure skin and clothing. This patent claims that basic agents need to be combined with "an absorptive insoluble filler material of emollient character, such as the stearate of zinc, aluminum or magnesium, or a mixture of talc and small portions of zinc oxide". The basic materials were said to lead to a drying action, which is offset by the healing action of the emollient. The patent does not prescribe deodorant formulations consistent with current understanding of mitigation of body odor due to perspiration.

While bases in high concentration may have "drying action", they primarily neutralize acids as is evident to those skilled in the art. The only "anti-acid" body listed in the claims, which if compatible with the body, is sodium bicarbonate. It is not capable of neutralizing the agents responsible for body odor.

The patent does not teach that if the formulations had any significant efficacy, it did not arise from the action of the basic agent, sodium bicarbonate, cited in the claim but from some other material or combination of materials. Metal stearates, the so-called "absorptive insoluble filler material of an emollient character" of the formulation, might, under some circumstances, be responsible for some, if any, activity associated with the formulation cited in this patent. Another possibility is zinc oxide, but it along with many other "basic" metal oxides like alumina are very unreactive against perspiration odor due to insolubility and low hydrolysis rate to a hydroxide form that could show some activity.

The filler materials are first and foremost sparingly soluble neutral metallic salts of a weak organic acid which would only be weakly hydrolyzed to a potentially active agent with the aluminum salt having the best potential for any efficacy due to its low hydrolysis pH.

The zinc salts would show some erratic behavior as noted before but would be strongly inhibited by being coupled to a weakly dissociated organic acid. The magnesium salt would be no more effective than Epsom salts since it has no capacity of generate basic deodorizing agent through dissolution in water.

The zinc stearate cited as the emollient could have some antiperspirant activity but is likely subject to the erratic activity noted earlier for zinc salts. The stearate portion could supply organic material to foster undesirable bacterial growth and therefore be undesirable.

U.S. Pat. No. 2,187,163 identifies the use of "base" carrier materials such as kaolin or calamine with the latter being preferred when combined with active deodorant materials such as aluminum and zinc chloride. Calamine, zinc oxide and sulphates of aluminum and zinc are claimed as active agents. It is said that these formulations supplanted with other agents such as tannic acid and/or salicylic acid "have the property of preventing or reducing perspiration and of acting as deodorants in this manner".

Oxides and carbonates of "acceptable" antiperspirant agents, such as alumina and calamine, are generally ineffective in reducing body odor because they are inactive with respect to the weak organic acid responsible for perspiration odor for reasons of equilibrium, kinetics and solubility. Sulphates of zinc, unlike those of aluminum, have been observed to be erratic performers likely because they do not hydrolyze effectively. The author claims that the sulphates of aluminum and zinc have the property of reducing or preventing perspiration and act as deodorants in this manner.

There is no evidence in the text to support this assertion and it is evident to those skilled in the art that neither compound would act to any significant extent as a desiccant. These agents most likely act in a different manner and understanding of the mechanism of this action could result in a significantly different approach in formulating materials with greater efficacy.

Body odor is known to those skilled in the art to be due primarily to the products of bacterial action and not moisture as such.

U.S. Pat. No. 3,996,346 cites zinc oxide and calcium hydroxide along with phenol as an effective deodorant. As is evident by the citation of U.S. Pat. No. 1,558,405, the use of lime as deodorant agent has been noted some time ago. Given the low activity of zinc oxide as a deodorant agent, it is likely that any observed deodorant activity is due to the lime. Lime is quite basic with reported pH's of 12.5 and higher. While lime has the capability to function as an effective agent against odor, it is less desirable than other agents due to its alkalinity. The zinc oxide combined with stearic acid as a cream base most likely is an attempt to minimize the undesirable effects due to high alkalinity and the general undesirable nature of phenyls in skin care products.

In summary, there is a wide range of active ingredients cited in the open and patent literature for prevention of body odor and perspiration but most have some undesirable characteristics. Many formulations use aluminum chloride or other aluminum compounds based on sulphates for example that form irritating acids. As well, human exposure to aluminum is raising health concerns. Other formulations recommend materials, such as potassium carbonate, that can be harmful to the skin, or salts of zinc that have minimal efficacy due to poor hydrolysis to active hydroxide.

There is, therefore, a need to bring forward alternative deodorant formulations that balance the need for performance, efficacy, simplicity, and compatibility of the formulation with good health care in conjunction with a technically sound understanding of the reason for body odor and therefore the correct abatement measures to take.

SUMMARY OF THE INVENTION

This invention aids in fulfilling these needs in the art by providing a deodorant composition consisting essentially of magnesium hydroxide. One embodiment of the invention involves a composition, wherein the magnesium hydroxide is applied as a 1% to 10% by weight slurry made from alcohol and water, with the alcohol content preferably being in the range of about 5% to about 25% by weight. The slurry is preferably applied with a pump applicator.

In another embodiment of the invention, the magnesium hydroxide is used as the active agent in other types of applications, such as aerosols, powders, sticks, roll-ons, and the like, with emollients or fragrances.

In still another embodiment of the invention, the deodorant agent consists essentially of magnesium hydroxide and zinc hydroxide. In an alternative embodiment, the zinc hydroxide and magnesium hydroxide are combined such that the magnesium hydroxide is present in a molar excess.

This invention also provides a method of reducing human perspiration odor, wherein the method comprises applying to a surface in contact with human perspiration a composition consisting essentially of magnesium hydroxide, and optionally zinc hydroxide, in an amount sufficient to thereby reduce the perspiration odor. For example, the composition can be applied to the skin of a human in contact with the perspiration.

Further, this invention provides a method of reducing perspiration odor on a human, wherein the method comprises applying to the human an aqueous composition consisting essentially of magnesium hydroxide in an amount sufficient to neutralize 3-methyl-2-hexanoic acid to thereby reduce the perspiration odor. Zinc hydroxide can optionally be incorporated in the composition with the magnesium hydroxide. The composition can be applied to the underarm of a human to control perspiration odor.

DETAILED DESCRIPTION OF THE INVENTION

There are problems associated with the active agents used in many deodorant formulations as noted in the prior art. In searching for a suitable formulation, the objective has been to find an agent or agents that acted as deodorants rather than antiperspirants. However, it will be evident to those skilled in the art that an agent effective as a deodorant could well be part of the basis for an antiperspirant formulation using materials obvious to those skilled in the art for the purpose of combating wetness.

It is now known that certain organic acids, such as 3-methyl-2-hexanoic and others reported by George Preti of the Monell Chemical Senses Center in Philadelphia, are primarily responsible for offensive body odors generally associated with perspiration. These acids are produced by microorganisms.

Therefore, antibacterial agents such as cited in the prior art may inhibit bacterial growth and diminish body odor, but since bacteria mutate so readily increasingly potent agents may well be needed and the potency required could harm the skin or cause systemic damage in the case of organic antibacterial agents.

Antiperspirant agents can also minimize the problem by maintaining a dry environment and minimizing growth of the bacteria, but agents capable of maintaining the requisite dryness could also damage the skin.

One solution is to simply neutralize the acid produced and thereby eliminate the odor of the acid by forming a salt of the hexanoic acid with a suitable base. Strong bases cited in the prior art, such as potassium carbonate, are no good because they are so basic that they cause skin damage and they are also so soluble that they rapidly wash away under heavy perspiration providing a very low duration of protection.

Agents that effectively neutralize the above hexanoic acid have been found to eliminate the odor associated with perspiration and in doing so explain why many of the agents cited in the prior art had some degree of efficacy.

Conventional basic agents need to yield a pH of 9 to 10 as a minimum to be effective but not extend much above this level to avoid skin irritation. The base must behave in such a manner that it does not wash away like soluble carbonates or more simply, the base should be sparingly soluble and with the requisite pH requirements, function on a stand alone basis, and not be harmful to the skin.

At the same time, a metal hydroxide base is preferred due to its high activity compared to metal carbonates, such as limestone or other such benign carbonates, when trying to neutralize a weak organic acid. As well, a metal hydroxide is preferred over metal oxides since many show very low solubilities and negligible reactivities like alumina. Lime has been previously identified as a deodorant ingredient, but its high pH rules out direct application.

A suitable and simple agent not cited before is magnesium hydroxide, commonly termed milk of magnesia, which has been used for medicinal purposes of some considerable time. It has low solubility and therefore does not "wash away" under heavy perspiration. The pH is in the range of 10.0 and magnesium hydroxide provides 16–20 hour protection and more for a broad cross section of people.

The magnesium hydroxide can be incorporated in a composition of the invention for controlling perspiration odor such that the composition has a pH of about 9 to about 10.5. Preferably, the pH of the composition is about 10. Zinc hydroxide can be incorporated in the composition with the magnesium hydroxide. In this event, the composition typically has a pH of about 7.5 to about 10.5, preferably about 9 to about 10. The zinc hydroxide typically lowers the pH of the magnesium hydroxide-containing perspiration odor-controlling composition of the invention.

The composition of the invention is most conveniently dispensed as a 2-5% suspension with a mixture of 20% ethyl alcohol and 80% water.. The ethyl alcohol acts as a dispersant for the magnesium hydroxide, as well as the zinc hydroxide if present. In addition, the ethyl alcohol aids drying of the composition on the surface to which the composition is applied, thus avoiding extended wetness. It has also been found that ethyl alcohol aids in minimizing clogging of spray nozzles when the composition is sprayed onto a surface. Thus, it will be understood that other materials that perform the functions associated with the ethyl alcohol can be used in combination with ethyl alcohol or substituted for the ethyl alcohol. Typically, about 1% to about 5% by weight magnesium hydroxide is formed in an aqueous slurry containing about 5% by weight to about 25% by weight of an alcohol.

Although it may seem evident after an overview of the chemistry of acids, bases, salts, hydrolysis theory and the theory of odor due to perspiration, the use of magnesium hydroxide has not been identified before possibly because a detailed understanding of the multiple phenomena involved have not been laid out in a coherent fashion.

Metal hydroxides are the most active agents against body odor, and another agent not previously identified is zinc hydroxide, which is active even though it is more neutral than milk of magnesia. As well, zinc has a well known salutary effect on the skin. Several deodorant formulations use zinc oxide; however, as noted before, of the group of metal oxides that could be considered safe for human use, most hydrate to the active hydroxide form very slowly. For example, as in the Bayer aluminum process, strong caustic soda is required to transform alumina to the hydroxide form in high yield.

While zinc oxide is not as difficult to hydrate, even strongly basic oxides, such as magnesium, require significant time to hydrolyze. Therefore, by far the best form for application is zinc hydroxide since it has active and available hydroxide.

Sulphates and chlorides of zinc hydrolyze to zinc hydroxide in an erratic manner because the protolysis reaction is much less extensive than with aluminum chloride or potassium alum, for example.

Greenwood and Earnshaw refer to metal salt hydration as hydrolysis or protolysis reactions having some similarity to acidity scales. The literature, such as Chemical Reviews 1957 and Progress in Physical Organic Chemistry, document a variety of acidity and basicity scales based not only on the pioneering work of Louis P. Hammett but concepts such as carbon acidity and basicity.

Ralph G. Pearson proposed in 1966 (Journal of the American Chemical Society) a very broad concept of acids and bases called HSAB that went beyond the Bronstead and Lewis theory of acids and bases to include a wider range of phenomena that cover the concept of cation acidity, which can be used, in conjunction with solubility phenomena, to rationalize protolysis reactions as observed with salts such as aluminum chloride.

With an absorber such as body oils, HCl from aluminum chloride hydrolysis is absorbed. The aluminum cation is so "acidic" that it reacts with water as a "base" and forms aluminum hydroxide which can then neutralize hexanoic acid. At the other end of the scale, a salt like magnesium sulphate has a magnesium cation that cannot "hydrolyze" or has insufficient cation acidity to form magnesium hydroxide, and consequently cannot act as an effective deodorant. The formal hydroxide form of magnesium must be used for deodorant purposes.

Salts of the zinc do not have enough cation acidity to form zinc hydroxide to any effective degree except to the extent that most soaps impart some alkalinity causing the formation of zinc hydroxide. Hence the sporadic action of zinc salts and the need to use zinc hydroxide as a deodorant rather than zinc salts.

However, pure zinc hydroxide can be sticky and uncomfortable although not to the extent that zinc oxide is. In addition, hydroxides of increasing cation acidity like zinc can dry and form inactive oxides. Therefore, an effective formulation for zinc hydroxide is to mix it with magnesium hydroxide with preferably a mole excess of magnesium hydroxide. This ensures that the zinc stays in the active hydroxide form and does not dehydrate to a relatively inactive oxide form. This formulation, incorporates salutary aspects of zinc.

More particularly, when the magnesium hydroxide is combined with zinc hydroxide to form the odor-controlling composition of the invention, the molar ratio of magnesium hydroxide to zinc hydroxide can be varied over a relatively wide range. The molar ratio will typically be up to about 3 mols of magnesium hydroxide to 1 mol of zinc hydroxide, and preferably the molar ratio will be up to about 1.5:1. In a particularly preferred embodiment of the invention, the magnesium hydroxide is employed in a molar excess relative to the zinc hydroxide and is in a molar ratio up to about 1:1. In any event, the magnesium hydroxide is employed in an amount sufficient to maintain the zinc in the hydroxide form.

It proposed that this phenomena occurs since the zinc is a more acidic cation than magnesium as noted earlier and in the same sense that magnesium is a more acidic cation than calcium. Those skilled in the art will recognize that this phenomena is demonstrated in the production of magnesium whereby magnesium chloride is converted to magnesium hydroxide by the addition of lime.

The above formulations of magnesium and zinc can require moisturizing agents to ensure that there is available hydroxide in solution on the skin's surface. Neutral salts are preferred with lower solubilities being favored. Examples of suitable moisturizing agents are Epsom salts, Glaserite, and kainite.

The composition of the invention can also contain a nontoxic, non-corrosive, double salt having water of hydration and a pH of about 5 to about 8 when dissolved in water. The double salt is employed in an amount sufficient to increase retention of the magnesium hydroxide, and zinc hydroxide if present, on the surface to which the composition is applied in the presence of human perspiration. The double salt thus aids in minimizing the likelihood that the composition of the invention will "wash away" in the presence of heavy perspiration.

The composition of the invention can be applied to a surface in contact with human perspiration. Thus, for example, the composition can be applied to the skin of a human, such as the underarm or foot areas. As another example, the composition can be applied to a garment in contact with perspiration, such as a sock or shoe.

The admixture of zinc and magnesium hydroxides has yielded deodorant protection for extended periods of time ranging upwards of three days. Formulations like this capable of providing protection against body odor not only demonstrate the efficacy of the product but do have specific applications for whole body protection with say hunters or naturalists who want assistance in eliminating body odor to closely approach wildlife reactive to human scent.

It is evident to those skilled in the art that there are other materials that would be effective as well. It is evident that metallic chlorides, nitrates and sulphates can present problems due to acid formation upon metal hydrolysis to a hydroxide. The most suitable agents would be based on metal carbonates with hydrolysis points in acidic pH range. Any acid produced by the metal carbonate hydrolysis would form harmless carbon dioxide.

While the author is not bound by the above concepts, they do offer an operational understanding of the complex phenomena involved.

What is claimed is:

1. A deodorant composition consisting essentially of zinc hydroxide and magnesium hydroxide in a sufficient an effective deodorant amount to neutralize 3-methyl-2-hexanoic acid associated with human perspiration and to maintain the zinc hydroxide in active hydroxide form, together with an acceptable carrier, wherein the magnesium hydroxide and zinc hydroxide are present in a molar ratio up to about 3:1.

2. The composition as claimed in claim 1, comprising about 1% by weight to about 10% by weight magnesium hydroxide in an aqueous slurry containing about 5% by weight to about by weight of an alcohol.

3. The composition as claimed in claim 1, wherein the composition comprises an effective amount of a moisturizing agent to ensure available hydroxide in solution.

4. The composition as claimed in claim 3, wherein the moisturizing agent is selected from the group consisting of Epsom salts, Glaserite, and kainite.

5. The composition as claimed in claim 1, wherein magnesium hydroxide and zinc hydroxide are present in a molar ratio up to about 1:1.

6. The composition as claimed in claim 1, wherein magnesium hydroxide is present in a molar excess up to an amount of about 1.5:1 relative to the molar amount of zinc hydroxide.

7. The composition as claimed in claim 1, wherein the composition has a pH of about 9 to about 10.5.

8. The composition as claimed in claim 6, wherein the composition has a pH of about 7.5 to about 10.5.

9. A method of reducing perspiration odor on a human, wherein the method comprises applying to the human an aqueous composition consisting essentially of magnesium hydroxide in an amount effective to neutralize 3-methyl-2-hexanoic acid to thereby reduce said perspiration odor.

10. The method as claimed in claim 9, wherein said composition is applied to the underarm of the human.

11. The method of reducing human perspiration odor, wherein said method comprises applying to the skin of a human in contact with said perspiration a deodorant composition as claimed in claim 1.

12. A deodorant composition consisting essentially of about 1% to about 5% by weight magnesium hydroxide formed in an aqueous slurry containing about 5% to 25% by weight of an alcohol.

13. The composition as claimed in claim 12 wherein the slurry comprises 2% to 5% by weight magnesium hydroxide, 20% ethyl alcohol, and 80% water.

14. The composition as claimed in claim 12, wherein the composition comprises zinc hydroxide and magnesium hydroxide in an effective deodorant amount to maintain the zinc hydroxide in active hydroxide form, together with an acceptable carrier, and wherein the magnesium hydroxide and zinc hydroxide are present in a molar ratio up to about 3:1.

* * * * *